(12) United States Patent
Mujwid et al.

(10) Patent No.: US 7,255,703 B2
(45) Date of Patent: Aug. 14, 2007

(54) VARIABLE-AXIS SURGICAL DRIVER

(75) Inventors: James R. Mujwid, Crystal, MN (US); Thomas J. Gisel, Chaska, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 253 days.

(21) Appl. No.: 10/821,298

(22) Filed: Apr. 9, 2004

(65) Prior Publication Data

US 2005/0015097 A1 Jan. 20, 2005

Related U.S. Application Data

(60) Provisional application No. 60/461,742, filed on Apr. 10, 2003.

(51) Int. Cl.
*A61B 17/56* (2006.01)

(52) U.S. Cl. .................................................. 606/104

(58) Field of Classification Search .............. 606/86, 606/99, 104; 173/215, 213, 221, 170
See application file for complete search history.

(56) References Cited

U.S. PATENT DOCUMENTS

| | | | |
|---|---|---|---|
| 4,501,269 A | 2/1985 | Bagby | |
| 4,522,270 A * | 6/1985 | Kishi | 173/217 |
| 5,329,834 A * | 7/1994 | Wong | 81/58.3 |
| 5,797,918 A | 8/1998 | McGuire et al. | |
| 5,904,689 A * | 5/1999 | Jonjic | 606/99 |
| 6,467,556 B2 * | 10/2002 | Alsruhe | 173/217 |
| 6,830,574 B2 * | 12/2004 | Heckele et al. | 606/104 |
| 2001/0021853 A1 | 9/2001 | Heckele et al. | |

FOREIGN PATENT DOCUMENTS

| | | |
|---|---|---|
| DE | 10220190 | 10/2001 |
| EP | 1234637 | 8/2002 |

OTHER PUBLICATIONS

"Laparoscopic 4050 Surgical Technique BAK™ Interbody Fusion System," *Sulzer Spine-Tech, SulzerMedica*, pp. 1-31 (Aug. 2000).

* cited by examiner

*Primary Examiner*—Eduardo C. Robert
*Assistant Examiner*—Michael J. Araj
(74) *Attorney, Agent, or Firm*—Wood, Herron & Evans, LLP (57) ABSTRACT

A surgical driver for use with an implant, having a shaft with proximal and distal ends and an attachment piece with proximal and distal ends. The surgical driver including a coupling arrangement that couples the shaft and the attachment piece relative to one another. The coupling arrangement includes a recess formed at the proximal end of the attachment piece and has at least one retaining member for reversibly engaging the shaft. The coupling arrangement is adapted to accommodate interaction between the surgical driver and an implant so that variable-axis torque on the implant is minimized.

21 Claims, 13 Drawing Sheets

VARIABLE-AXIS SURGICAL DRIVER

CROSS REFERENCE TO RELATED APPLICATIONS

This application claims the benefit of U.S. Provision Application No. 60/461,742 filed on Apr. 10, 2003; which application is incorporated herein by reference.

TECHNICAL FIELD

The invention relates generally to orthopedic implants, and specifically to an apparatus for and method of inserting the implants.

BACKGROUND

An intervertebral disc is a pad of cartilage-type material situated between spinal bones. Each disc serves as a connector, spacer, and shock absorber for the spine. A soft, jelly-like center is contained by outer layers of fibrous tissue. Healthy discs facilitate normal turning and bending. Trauma or injury to the spine can cause discs to tear, bulge, herniate, and even rupture. This can be quite painful, as the soft center of the disc leaks, putting pressure on the adjacent nerve roots and spinal cord.

A damaged disc can cause nerve dysfunction and debilitating pain in the back, legs and arms. Typical treatments that provide relief and allow patients to function again include back braces, medical treatment, physical therapy and/or surgery to remove the disc.

A conventional surgical solution removes the injured or degenerated disc and promotes new bone growth in the space to fuse the adjacent vertebrae. Such surgery can be highly invasive and may require two relatively large incisions. A first incision may be made in the front of the body so that the damaged disc can be removed. The second incision may then be made in the back so that, for example, connecting rods and anchor screws can be attached to the vertebrae to stabilize them long enough for the new bone to grow. This type of surgery typically results in recovery periods that can extend as long as six months.

For the purpose of achieving long term stability in a segment of injured spine, a fusion (the joining together of two or more bones via a continuous bridge of incorporated bone) may be performed. Interbody fusion, wherein the disc is partially excised and bone placed within the space previously occupied by the excised disc material (between adjacent vertebrae), is one typical type of fusion. Interbody fusion is performed for the purpose of restoring a more "normal" spatial relationship, and to provide for stability; short term by mechanical support, and long term by the permanent growth of bone from vertebra to vertebra.

For fusion to occur within the disc space, in certain procedures, it is necessary to prepare the vertebrae to be fused by penetrating, or cutting into, the hardened outside cortical plates of bone (the endplates) to allow an interposed bone graft to come into direct contact with the more vascular cancellous (spongy) bone, and to thereby stimulate the body to heal this induced, but controlled, "injury" by both bone production and "creeping substitutions" of the graft to create a continuous segment of bone between the opposed vertebral surfaces.

Following the removal of a damaged disc, if an implant, such as a bone graft, is not placed in the intervertebral space, collapse may occur, which may result in damage to the nerves; or the space may fill with scar tissue and eventually lead to a reherniation. However, the use of bone to fill the space is sometimes suboptimal because bone obtained from the patient requires additional surgery and is of limited availability, and if obtained from another source, lacks living bone cells, carries a risk of infection, and also is limited in supply. Furthermore, regardless of the source of the bone, it may have marginal biomechanical characteristics and may lack means to either stabilize itself against dislodgement or to stabilize the adjacent vertebrae.

There have been extensive attempts to develop an acceptable disc prosthesis (an artificial disc). Such devices would be used to replace a damaged disc, to restore the height of the interspace, and to restore the normal motion of that spinal joint. Examples include a flexible disc implant, a flexible disc replacement with file-like surface projections to discourage dislocation, and a bladder-like disc replacement with two opposed stud-like projections. Although such devices are placed within the intervertebral space following the removal of a damaged disc, they may result in eventual fusion or fixation of the spine.

Related to disc prosthetics are those devices used to replace essentially wholly removed vertebrae (e.g., corpectomy devices). Such removal is generally necessitated by extensive vertebral fractures, or tumors, and is not associated with the treatment of disc disease. Due to the removal of the entire vertebra, intervertebral disc-replacements are not feasible. Therefore, these implants perform as temporary structural members mechanically replacing the removed vertebrae (not removed disc), and do not intrinsically participate in supplying osteogenic material to achieve cross vertebrae bony fusion. Typically, use of these devices will be accompanied by further surgery consisting of a bone fusion procedure using the conventional techniques.

Similarly, other devices are designed to be placed within the vertebral interspace following the removal of a damaged disc, and seeking to eliminate further motion at that location. One such device is contained in U.S. Pat. No. 4,501,269 issued to Bagby, which describes an implantable device and instrumentation. The method employed is as follows: a hole is bored transversely across the joint, a hollow metal basket of larger diameter than the hole is impacted into the hole, and the hollow metal basket is filled with the bone debris generated by the drilling.

Implants such as those disclosed in the Bagby patent were impacted against resistance to achieve vertebral distraction, and were, therefore, susceptible to forceful dislodgement by the tendency of the two distracted vertebrae to return to their original positions, squeezing out the device. Conversely, the next generation of devices approved by the FDA and sold commercially were threaded cylinders, usually referred to as "cages". These cages typically are manufactured from biocompatible metals, such as titanium. These implants, are typically screwed into place. Because no unscrewing force exists between the vertebrae, compression alone cannot dislodge the implant. The implant is, therefore, more stable.

Spinal implants having threaded cages facilitate a less traumatic insertion into the intervertebral space. Such devices can be securely screwed into place, and often possess highly specialized locking threads to make accidental dislodgement impossible. Because of the proximity of the spinal cord, spinal nerves, and blood vessels, any implant dislodgement might have catastrophic consequences.

An implantation procedure involves numerous steps. According to one method of implantation, these steps may include the presurgical measurement of the vertebrae, selection of an appropriate implant size, and determination of a desired distraction of the vertebrae in order to achieve a desired alignment of the spine. A discectomy or partial discectomy also may be performed, removing part or all of the disc. Alternatively, no disc material need be removed. Incisions and retractions are performed to expose the injured area of the spinal column. A distractor is then inserted and impacted into the intervertebral space. After distraction, a surgical tube is positioned over the implant area. Once a hole is drilled, various other steps are performed in order to tap (i.e., produce threads in) the adjacent vertebrae, for threading of the implant into the hole. It should be noted that these steps are merely a representative example of what may occur during an implantation surgery and individual steps may be altered or omitted, the order of the steps may vary and additional steps may be included in the process.

One exemplary implantation device that is currently in use is sold under the trade name BAK™ INTERBODY FUSION SYSTEM by Zimmer Spine Inc. (Minneapolis, Minn.). In this technique and apparatus, a hollow cage, about an inch long, is implanted through a small incision into the disc space between two vertebrae. The surgical invasion is highly reduced from the previous methods and patients recover much faster. In this method, the disc need not be removed entirely, but rather may be drilled out in two bilateral bores. An implant is placed in each bore space between the adjacent vertebrae to stabilize the spine. Morselized bone is harvested from the patient and packed inside the implant. Over time, new bone will fill the inside and outside of the implants and fuse the vertebrae. The degenerated disc need not be removed completely, because the bored out disc does not block the formation of new bone between two opposite sites on the adjacent vertebrae.

Figure 1:
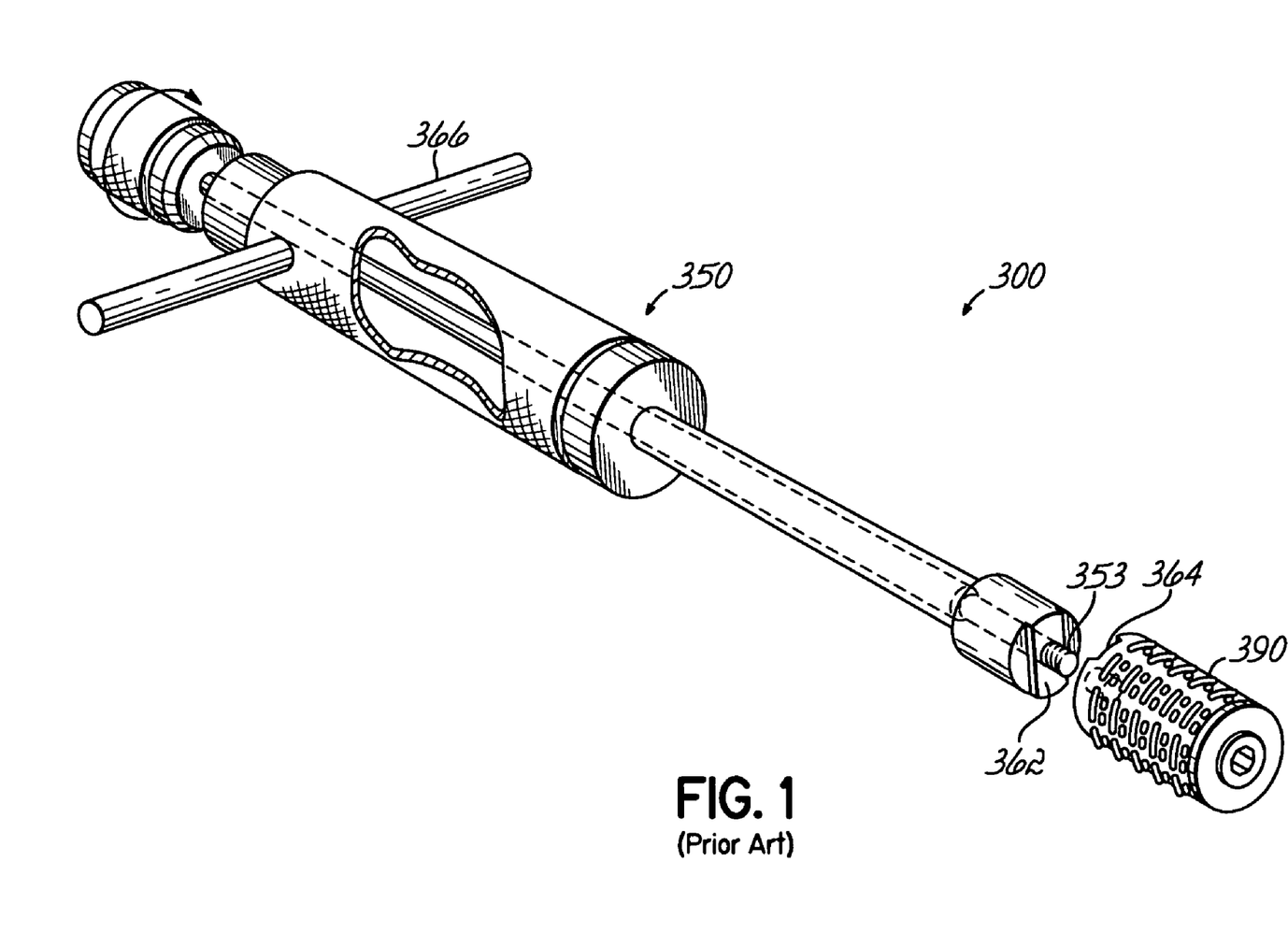
FIG. 1 is a perspective view of a prior art surgical driver and a prior art implant.

FIG. 1 shows a prior art surgical implant driver 300 having a handle 366 and a shaft 350. An implant 390 is attached to the distal end of the shaft 350 by means of a threaded portion 353. A protruding central area 362 on the distal end of the shaft 350 mates with a groove 364 of the implant 390 to ensure that the implant is not unscrewed from the threaded portion 353 when the driver is rotated.

Figure 2:
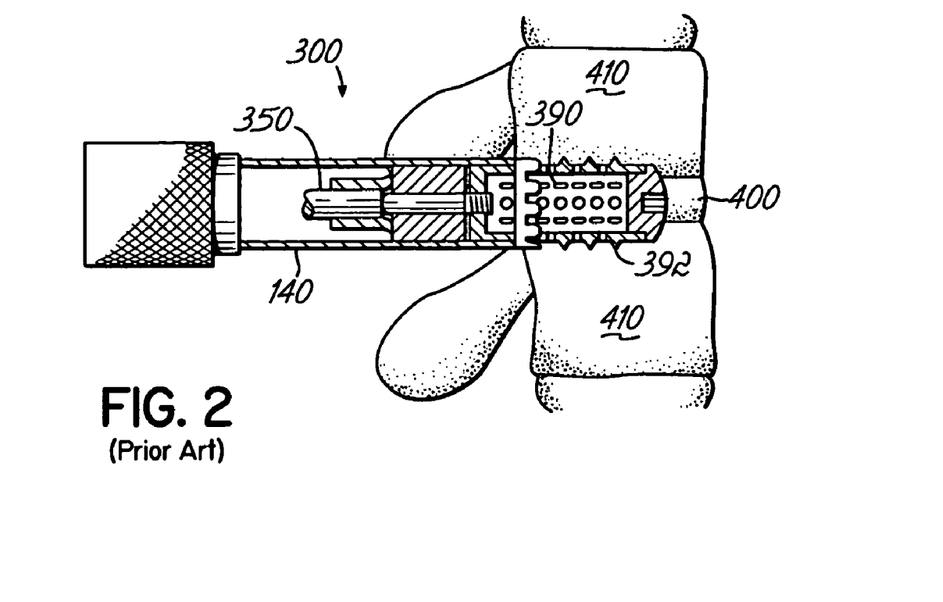
FIG. 2 is a side view of the prior art surgical driver of FIG. 1, showing a procedure of implanting the prior art implant into a vertebral column.
Figure 3:
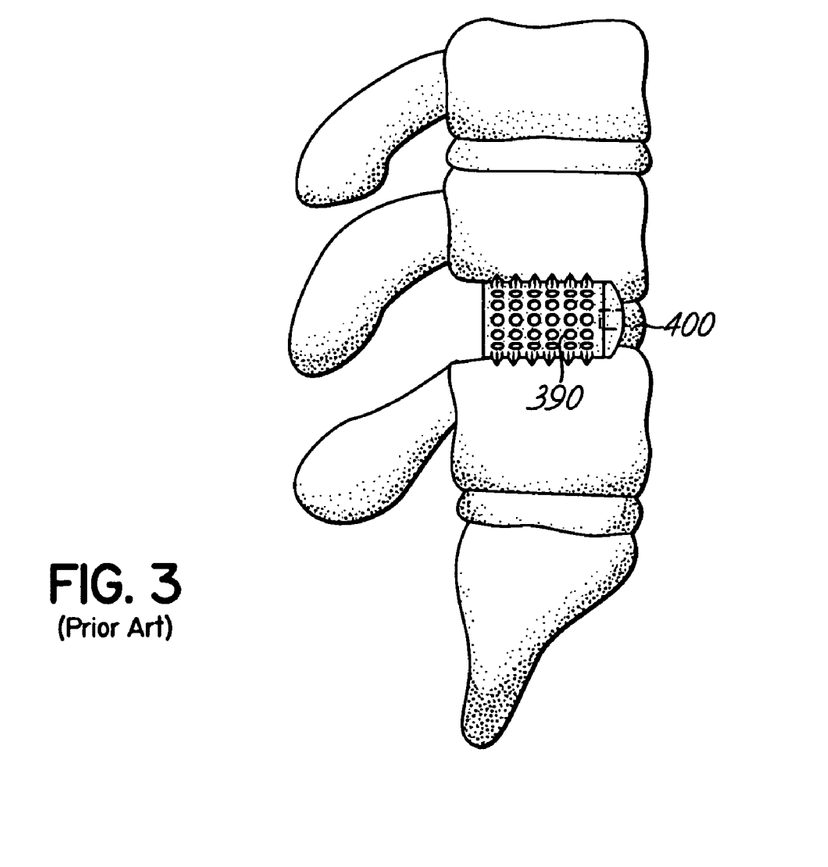
FIG. 3 is a side view of the vertebral column of FIG. 2 showing the implanted prior art implant.

As shown in FIG. 2, once a disc 400 and adjacent vertebrae 410 have been prepared for the implant 390, the shaft 350 of the driver is placed in a guide tube 140 that previously has been positioned in the appropriate location in the surgical area. After the implant 390 has traversed the surgical tube 140 and contacted the opening of the bore, the shaft 350 is rotated to align the threads 392 of the implant 390 with the threads cut into the vertebrae 410 as part of the implantation process. Further rotation of the shaft 350 screws the implant 390 into the bore until a desired depth has been reached. As shown in FIG. 3, the shaft 350 is detached from the implant 390 and the guide tube 140 is removed from its position in the surgical area, leaving the implant 390 in a predetermined intervertebral position. Because such implants often are installed in pairs, a similar procedure typically will be performed on the other side of the spine.

Although FIGS. 2-3 demonstrate a posterior implantation in the lumbar spine, spinal implants may be installed from other approaches. Furthermore, the implantation procedure may also be performed anteriorly or as a laparoscopic procedure.

Metal cages, although strong, are largely radiopaque. Because of this, the ability to detect fusion through diagnostic methodologies, such as x-rays, is greatly reduced with such devices. Radiolucent cages, made from polymers such as polyether ether ketone (i.e. PEEK), solve this problem. However, because such cages may not be as strong as those made of titatnium, there is an increased risk of fracture during implantation or removal, in the event that excessive torque loads are exerted on the implant. Accordingly, a need exists for a surgical driver that is better able to manage and direct these torque loads, in order to minimize the risk of implant fracture.

Because, in certain circumstances, significant force (e.g., torque) may be exerted on the implant during surgery, it is possible for implants to become deformed or break. In addition, such deformation or breakage will make the implantation or removal of the damaged implant difficult. As noted above, these challenges are exacerbated when radiolucent implants are used, because of their potentially reduced load bearing capacities as compared to titanium inserts. Common reasons for breakage may include misalignment of the implant, insufficient preparation of the implant hole, and/or improper connection to the surgical driver. For example, misalignments of the implant, relative to the implant bore and/or the driver may result in variable-axis forces being applied to the implant. Moreover, these conditions sometimes are difficult to detect and/or fully appreciate during surgery. Thus, because human operators will at times apply such variable-axis forces to the implant through a rigid surgical driver, such occurrences heretofore have not been completely eliminated. Accordingly, there exists a need to provide a surgical implant driver that will minimize the transmission of such variable-axis forces to the implant.

SUMMARY

One aspect of the present disclosure relates to a surgical driver for use with an implant. The driver includes an attachment piece and a shaft connected to the attachment piece by a coupling arrangement. The attachment piece includes mounting structure configured to engage an implant. The coupling arrangement is configured to transfer torque from the shaft to the attachment piece and permit the shaft to pivot relative to the attachment piece.

Another aspect of the present disclosure relates to a method of implanting an implant between two vertebral bodies. The method includes rotationally driving an implant between the two vertebral bodies with a driver having a shaft, the shaft being configured to axially pivot relative to the implant to reduce the likelihood of side torque applied to the implant.

Still another aspect of the present disclosure relates to a method of implanting an implant between two vertebral bodies, including mounting an implant to a surgical driver, rotationally driving the implant between the two bodies, and axially pivoting the shaft relative to the implant when side torque is applied to the shaft.

Yet another aspect of the present disclosure relates to a surgical system including a shaft connected to an attachment piece by a coupling arrangement, and an implant secured to mounting structure of the attachment piece. The coupling arrangement of the system transfers torque from the shaft to the implant and permits the shaft to pivot relative to the implant.

A variety of examples of desirable product features or methods are set forth in part in the description that follows, and in part will be apparent from the description, or may be learned by practicing various aspects of the disclosure. The aspects of the disclosure may relate to individual features as well as combinations of features. It is to be understood that both the foregoing general description and the following detailed description are explanatory only, and are not restrictive of the claimed invention.

DETAILED DESCRIPTION

The present invention, in one aspect, relates to a variable-axis surgical driver for reducing the risk of excess force (e.g., excess torque) application, implant breakage, and/or tissue injury during spinal implant surgery. As used herein, "variable-axis" refers to the ability to tilt at least one component of the driver in at least one plane, in relation to at least one other component of the driver, and/or in relation to the implant. Such a driver, advantageously, minimizes the transfer, to an implant, of variable-axis stresses exerted during manipulation by an operator.

Figure 4:
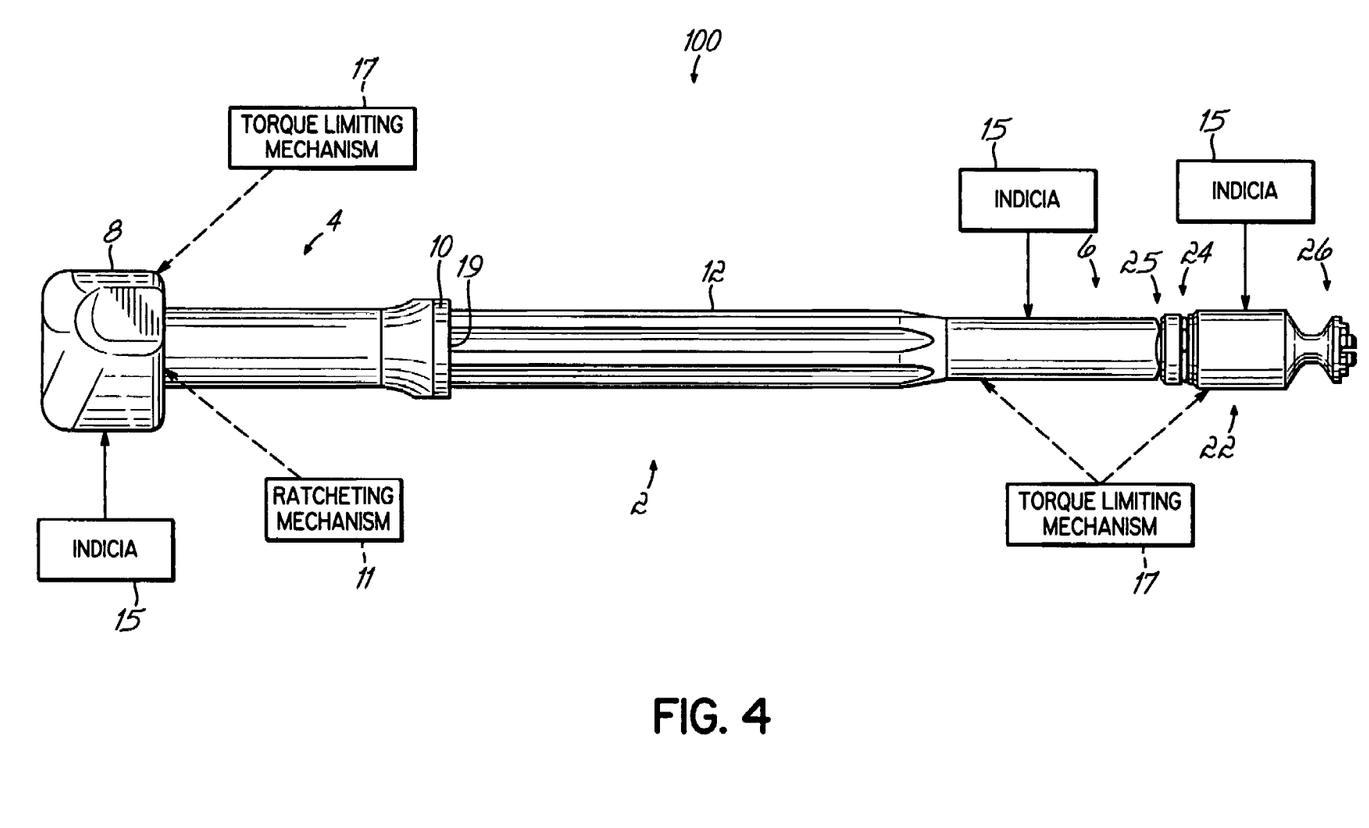
FIG. 4 is a side view of one embodiment of a surgical driver, in accord with the principles disclosed.

FIG. 4 shows one embodiment of a variable-axis surgical driver 100 in accord with the principles of the present disclosure. The surgical driver 100 comprises a first member or shaft 2 having a proximal end 4 and a distal end 6, and a second member or attachment piece 22, also having a proximal end 24 and a distal end 26. The proximal end 4 of the shaft 2 is adapted so that a handle 8 may be attached. In one embodiment, the handle 8 is detachable. The handle 8, if not permanently affixed to the proximal end 4 of the shaft 2, may connect by means of threads, an interference fit, or any other means known in the art. In one embodiment, the handle 8 includes a ratcheting mechanism 11 (represented schematically) that allow continuous rotation of the surgical driver 100 without necessitating release of the handle 8 by the operator. The ratcheting mechanism 11 may be of any type known in the art.

Figure 5:
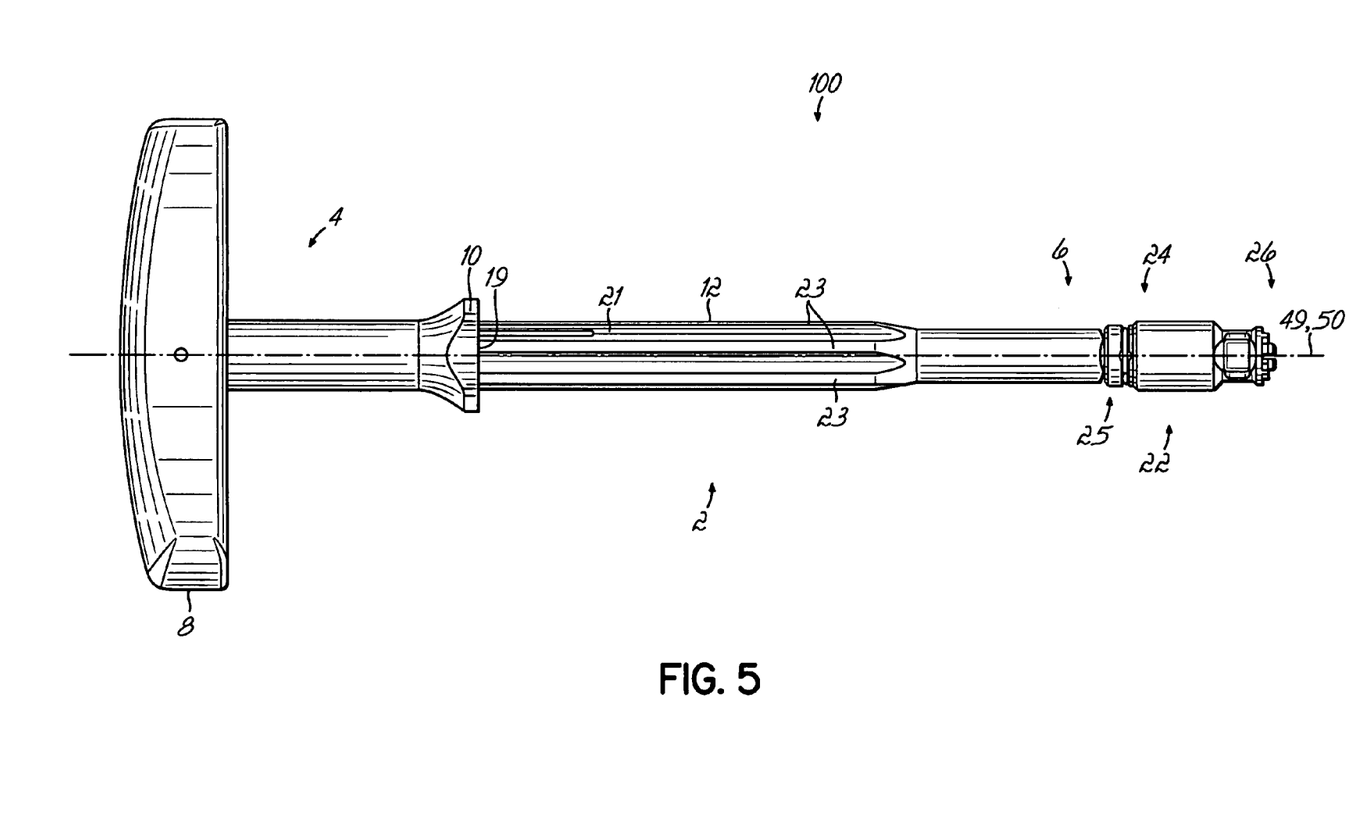
FIG. 5 is a top view of the surgical driver of FIG. 4.

The shaft 2 may have one or more indicia 15 (represented schematically), such as indexing flats, etched markings or other markings, positioned to indicate the orientation of an implant 200 (FIG. 13) during the surgical procedure. As shown in FIG. 5, the indicia 15 may be located on all, one, or a combination of the handle 8, the shaft 2, or the attachment piece 22. The shaft 2, attachment piece 22, or handle 8, also may include a torque limiting mechanism 17 (represented schematically). The torque limiting mechanism 17 can be used to provide a more precise determination and control of the amount of torque exerted on the implant 200 during a surgical procedure. The torque-limiting mechanism 17 may be of any type known in the art.

Referring now to FIGS. 4 and 5, a stop 10 is located on the shaft 2 of the surgical driver 100. Although the shape and position of the stop 10 may vary, in one embodiment a distal side 19 (the side facing the distal end 6) of the stop 10 will be flat and configured so as to prevent further progress of a sleeve 12 that may be installed from the distal end 6 of the shaft 2. The sleeve 12 may be integral with the shaft 2, or may comprise a separate member that is rotatable about a longitudinal axis 49 of the shaft 2. An outer surface 21 of the sleeve 12 may be provided with ridges 23 or other textures to facilitate manipulation of the device 100 and/or minimize mass. The sleeve 12, when used in conjunction with a surgical tube (not shown), advantageously provides improved stability and alignment during surgery. That is, the outer diameter of the sleeve 12 may be sized to correspond to an inner diameter of the surgical tube to axially guide the surgical driver 100 to the implantation site. A number of sleeves having varying sizes and yet all adapted to slide over the distal end 6 of the shaft 2 can be provided so that the surgical driver 100 can be used in a variety of surgical applications.

Figure 10:
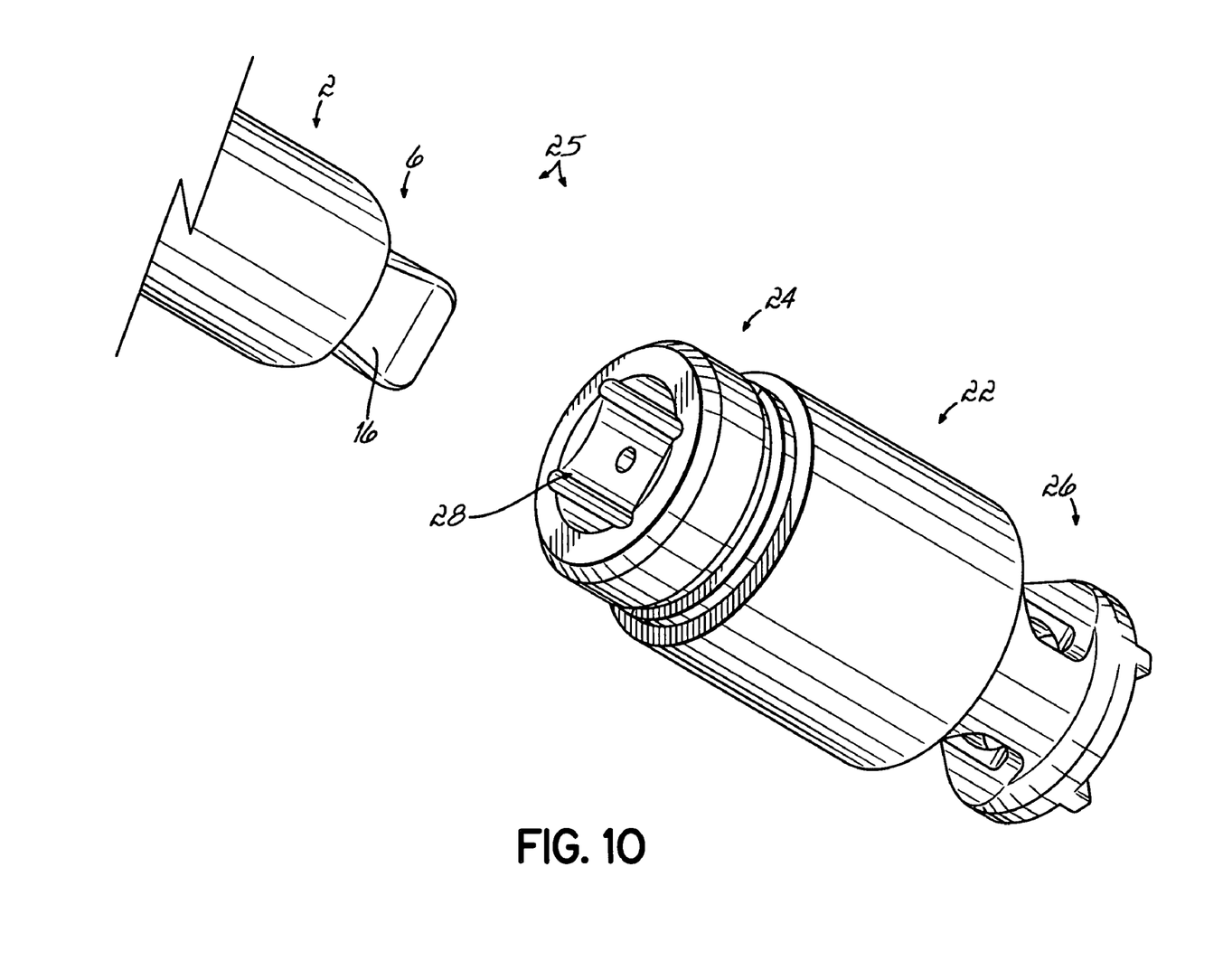
FIG. 10 is a perspective view of the distal end of the shaft member of FIG. 6 and the attachment piece of FIG. 7.
Figure 11:
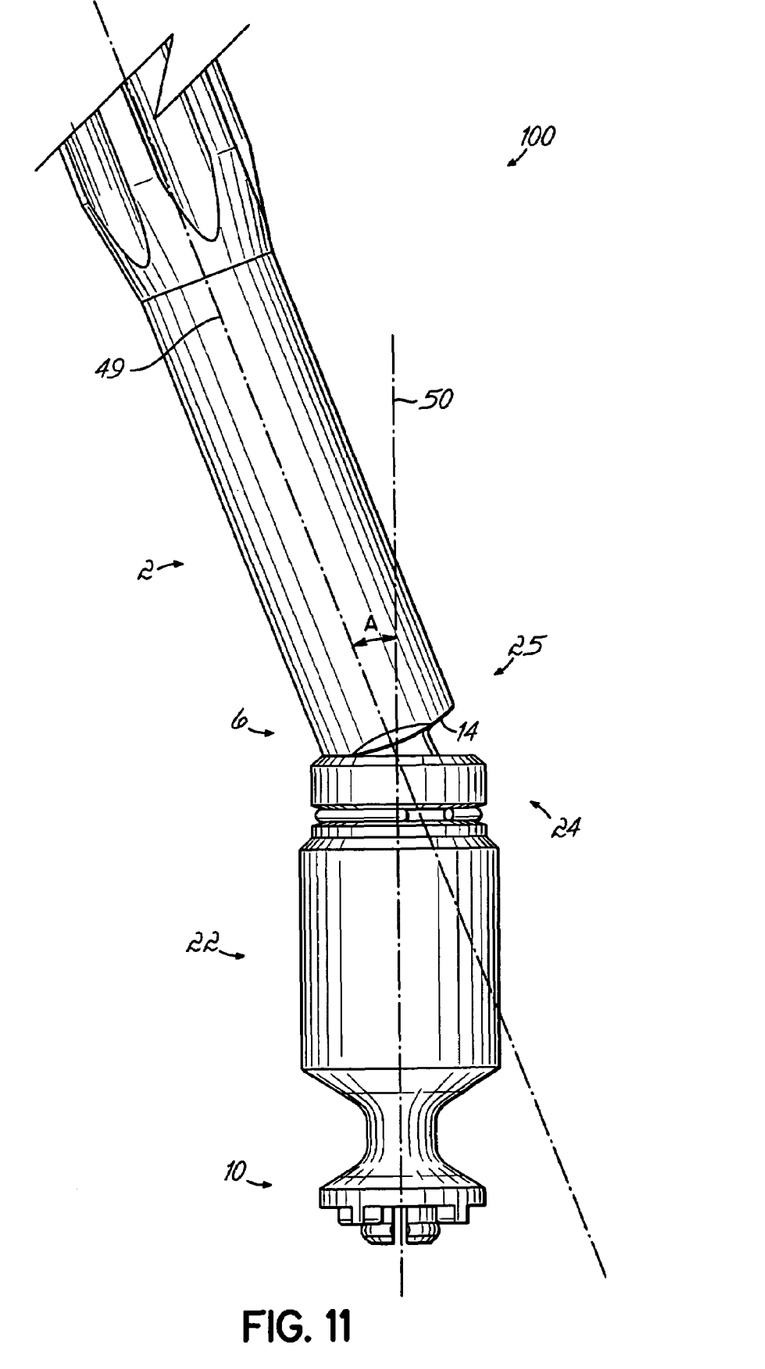
FIG. 11 is a partial, side view of the surgical driver of FIG. 4, shown in one of a plurality of axial orientations.

Referring now to FIGS. 10 and 11, the variable-axis surgical driver 100 includes a coupling arrangement 25. The coupling arrangement 25 operatively and reversibly couples the distal end 6 of the shaft 2 with the proximal end 24 of the attachment piece 22. What is meant by reversibly couple is that the shaft 2 may be selectively attached to and removed or detached from the attachment piece 22. Likewise, the proximal end 24 of the attachment piece 22 is adapted to operatively and releasably couple with the distal end 6 of the shaft 2.

Referring now to FIG. 11, the coupling arrangement 25 of the surgical driver 100 is configured such that each of the shaft 2 and the attachment piece 22 is movable with respect to the longitudinal axis of the other. That is, the shaft 2 may be pivoted, tilted, or moved in a range of axial orientations such that the longitudinal axis 49 of the shaft is no longer coxially aligned with a longitudinal axis 50 of the attachment piece 22. Likewise, the attachment piece 22 is moveable relative to the shaft 2. This angular freedom is achieved by the coupling interaction of the coupling arrangement 25 that occurs at the intersection of the distal end 6 of the shaft 2 and the proximal end 24 of the attachment piece 22. This angular freedom advantageously minimizes or prevents the transmission of excess and/or variable-axis forces to an implant 200 mounted to the distal end 26 of the attachment piece 22.

In particular, during use, forces are applied to the device 100 and transferred to the implant during an implantation procedure. If excessive side forces are applied to the surgical device 100, the shaft 2 of the device will pivot or axially angle relative to the implant and redirect the side forces to the attachment piece 22 rather than the implant. The pivoting movement of the shaft 2 indicates to the operator that excess side loading has been applied to the device. The operator can then re-orient the shaft 2 relative to the implant and continue with the surgical procedure accordingly, without having caused damage to the implant.

In the illustrated embodiment, the shaft 2 and attachment piece 22 are positionable in a plurality of axial orientations relative to one another about a 360-degree circumference. For example, the shaft 2 can be positioned or angled in an axial orientation relative to the attachment piece 22 in any direction. Also, the angular relationship between the longitudinal axes 49, 50 of the shaft and the attachment piece is preferably within an angular range A of between 1 and 30 degrees; more preferably between 15 and 20 degrees. In other words, the shaft 2 may be axially oriented between 1 to 30 degrees relative to the attachment piece 22 (and the implant 200) in any direction.

Figure 6:
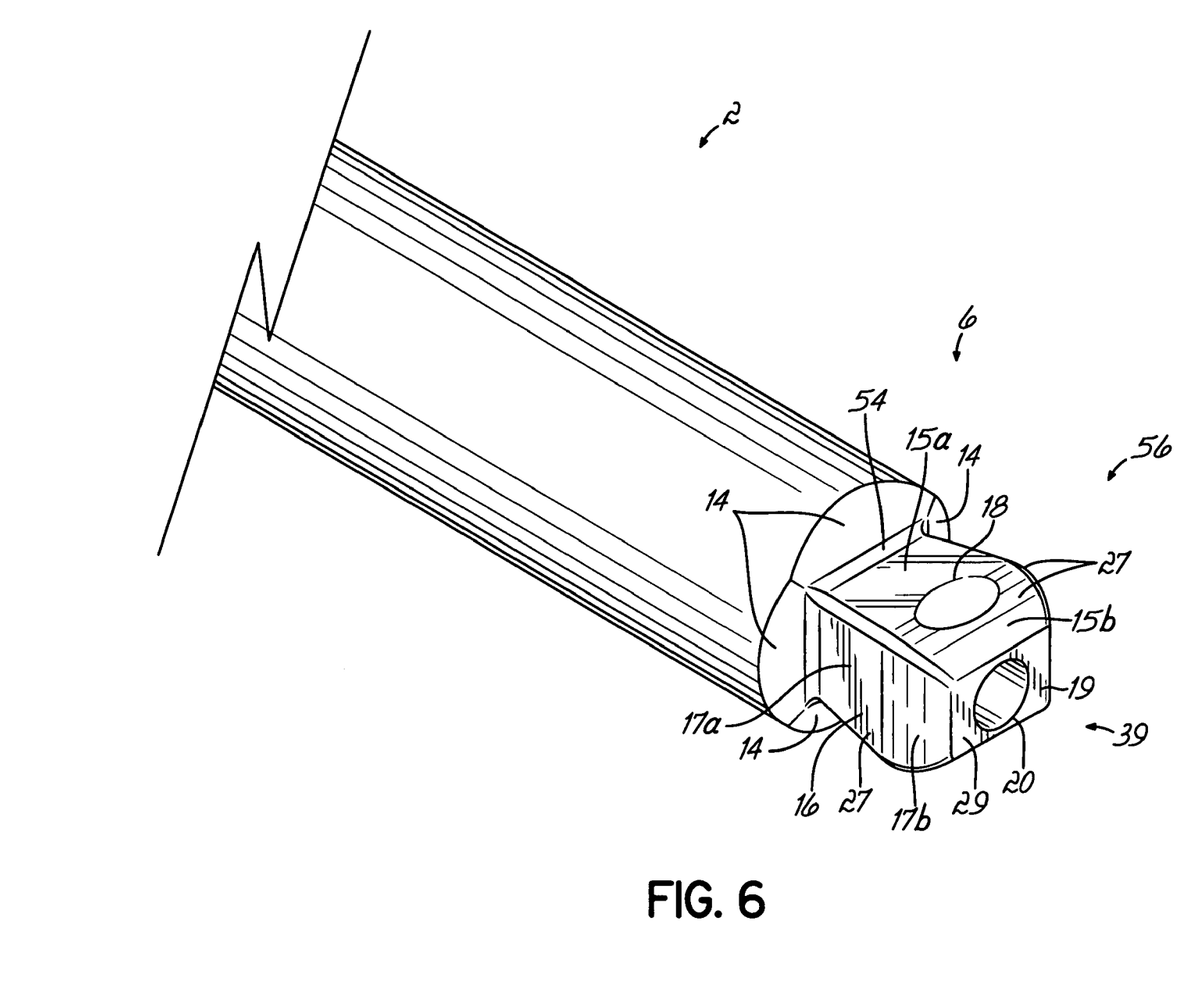
FIG. 6 is partial, perspective view of a distal end of a shaft member of the surgical driver of FIG. 4.
Figure 7:
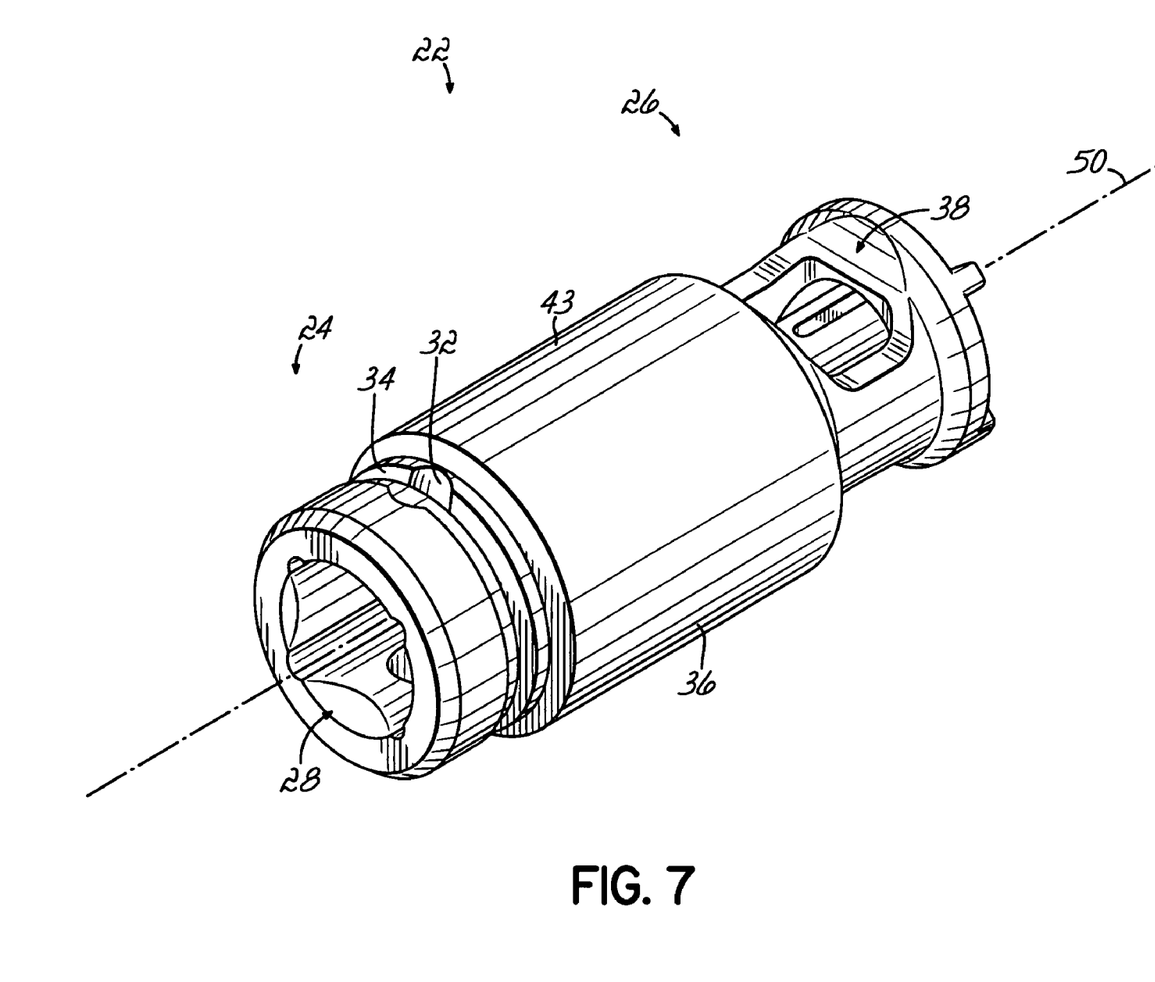
FIG. 7 is perspective view of a proximal end of an attachment piece of the surgical driver of FIG. 4.

Referring now to FIG. 6, an enlarged view of one embodiment of the distal end 6 of the shaft 2 is shown. The distal end 6 includes structure 56 to operatively and reversibly couple to the proximal end 24 of the attachment piece 22 (FIG. 7). In one embodiment, the structure 56 includes a knob 16. The term "knob" as used herein is used as a term of convenience to describe the structure of the distal end 6 of the shaft 2 and should not be construed as relating to any particular shape or configuration. The knob 16 may be formed as an integral part of the shaft 2, either molded or machined as one piece when the shaft 2 is constructed, or attached to the shaft 2 at a later time. The knob 16 may be of any shape, and in one embodiment, will have a generally rectangular cross-section. The rectangular cross-section advantageously provides the ability to determine the orientation of the implant 200.

In the illustrated embodiment, the knob 16 includes at least one indent 18 on at least one side 27 and may also have a hollow 20 formed on its distal face 29. In one embodiment, the indent 18 is elliptical to provide for a desired freedom of movement. Alternative geometries of the indent (e.g., elliptical, bilateral, unilateral, etc.) also may be utilized to provide a specific range of desired freedom of movement.

The distal end 6 of the shaft 2 includes one or more angled surfaces or facets 14 formed at or located adjacent to a base 54 of the knob 16 to allow for increased freedom of movement of the shaft 2 relative to the attachment piece 22, as will be described in detail below. In addition, one or more angled surfaces or facets 15a, 15b, 17a, 17b, 19 may be formed on the sides 27 of the knob 16.

Figure 8:
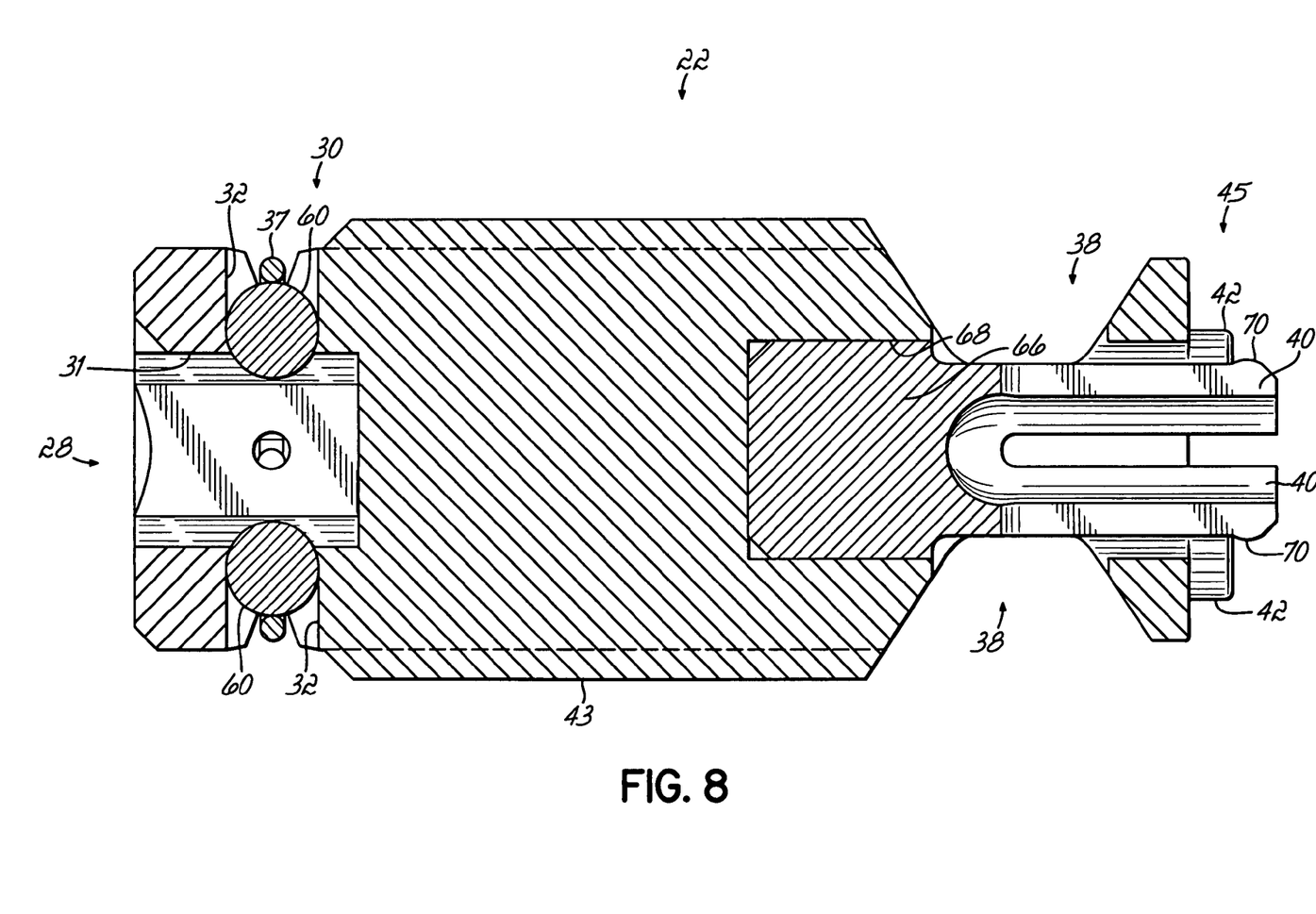
FIG. 8 is a cross-sectional view of the attachment piece of FIG. 7.

Referring now to FIGS. 7 and 8, the coupling arrangement 25 of the present disclosure includes a recess 28 formed in the proximal end 24 of the attachment piece 22. The shape of the recess 28 generally corresponds, at least in part, to the shape of the distal end 6 of the shaft 2 e.g. the knob 16. In the illustrated embodiment, the interior dimension of the recess 28 is slightly larger than the knob 16. The size and shape of the recess 28, in relation to the size and shape of the knob 16, is predetermined to provide a desired degree of angular freedom of movement to the shaft 2 when the distal end 6 is accommodated in the recess 28.

The coupling arrangement 25 also includes at least one retaining member 30 positioned in a sidewall 31 of the recess 28. The retaining member 30 is preferably moveable so that the shaft 2 can be releasably coupled to the attachment piece 22. In the illustrated embodiment, the retaining member 30 includes at least one ball 60. The ball is positioned within a bore 32 formed through the sidewall 31 of the recess 28. The bore 32 is sized so that a portion of the ball 60 protrudes or projects into the recess 28. As shown in FIG. 8, the retaining member 30 (e.g. ball 60) is captured by a snap ring 37 that encircles a majority of the circumference of the proximal end 24 of the attachment piece 22. The snap ring 37 is at least partially disposed within a groove 34 (FIG. 7).

The snap ring 37 movably maintains the retaining member 30 in a protruding position. The retaining member 30 also may be movably maintained in the protruding position by any other mechanism known in the art, including, but not limited to, springs or bands. The snap ring 37 is removable to permit the replacement or cleaning of the retaining member 30 and/or the use of snap rings having different tensions or spring-load characteristics, to achieve a desired biasing force against the retaining member 30.

The surgical driver 100 may include a centering arrangement or structure 39 that coaxially aligns the longitudinal axes 49, 50 of the shaft 2 and attachment member 22 when the shaft 2 is initially coupled to the attachment piece 22. In the alternative, the centering arrangement may be configured to align the longitudinal axes 49, 50 of the shaft 2 and the attachment 22 to a desired degree that is not coaxial.

Figure 12:
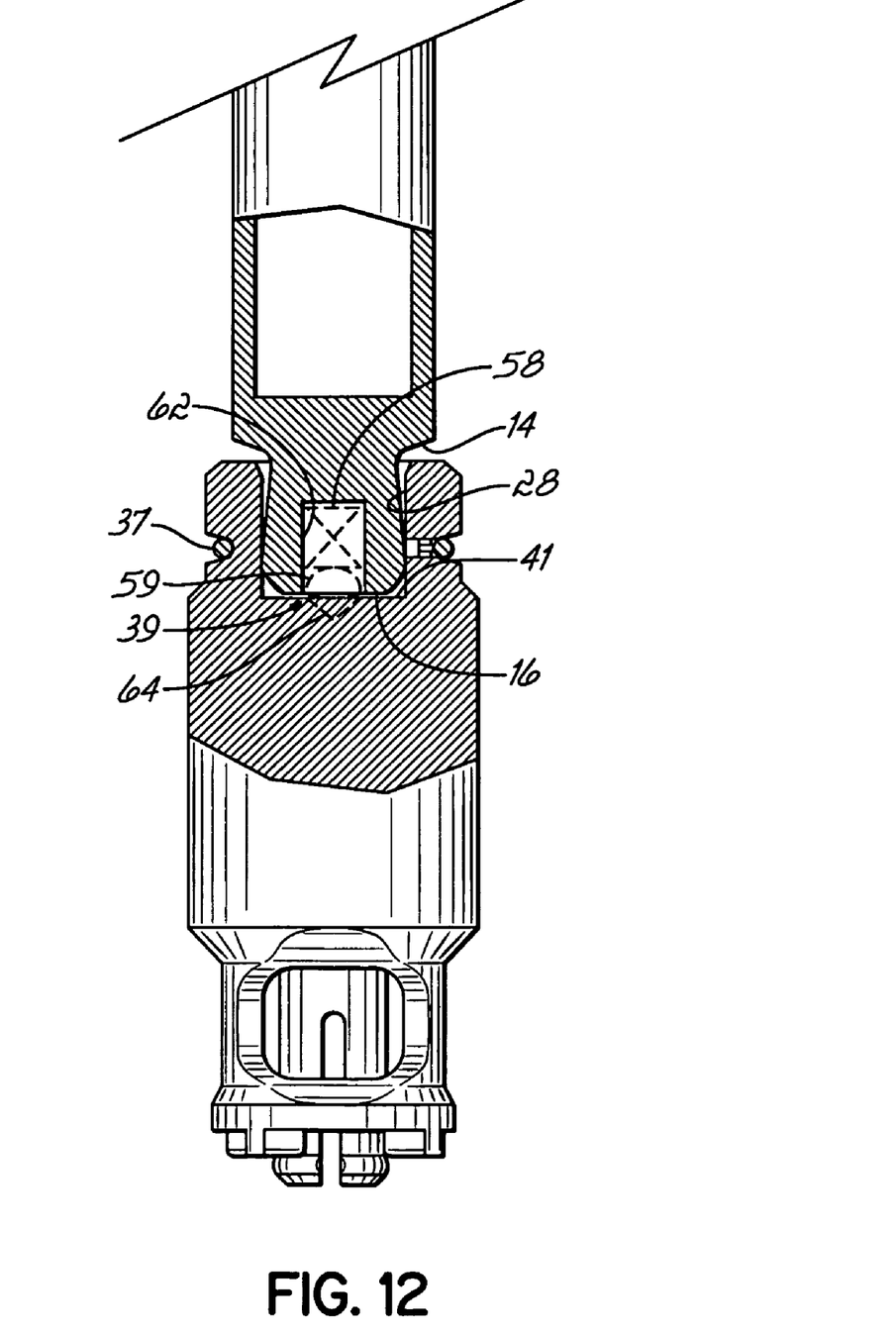
FIG. 12 is a partial, cross-sectional view of the surgical driver of FIG. 5.

Referring to FIG. 6, in one embodiment, the centering arrangement 39 includes the hollow 20 formed on the distal face 29 of the knob 16, and a corresponding projection (not shown) formed on a back surface 41 (FIG. 12) of the attachment piece 22 within the recess 28. The hollow 20 engages the corresponding projection within the recess to align the shaft 2 with the attachment piece 22. In another embodiment, shown in FIG. 12, the centering arrangement 39 (shown in dashed lines) includes a spring 58 positioned within a bore 62 formed in the end of the knob 16. The spring 58 biases a ball 59 outward from the end of the knob 16 (the ball 59 may be contained within the bore 62 by a forming process, for example). The ball 59 is arranged to engage a corresponding dimple or recess 64 formed in the back surface 41 of the attachment piece 22 to align the shaft 2 with the attachment piece 22.

Referring again to FIG. 7, the attachment piece 22 has an external surface 36 that may be integral with the attachment piece 22 or may form a separate piece. In one embodiment, the external surface 36 is a separate sleeve 43 (represented schematically by dashed lines in FIG. 8) that rotates about the longitudinal axis 50 of the attachment piece 22. The rotatable sleeve 43 will advantageously provide an area for gripping that need not be released by the operator as the surgical driver 100 is rotated. In one embodiment the external surface 36 is removable. The removable external surface 36 will advantageously allow for the cleaning of both the attachment piece 22 and the interior of the external surface 36. Although the illustrated external surface 36 of FIG. 7 is solid, in alternative embodiments the external surface 36 may comprise openings (not shown) in order to reduce mass and facilitate cleaning or assembly of the attachment piece 22.

Figure 9:
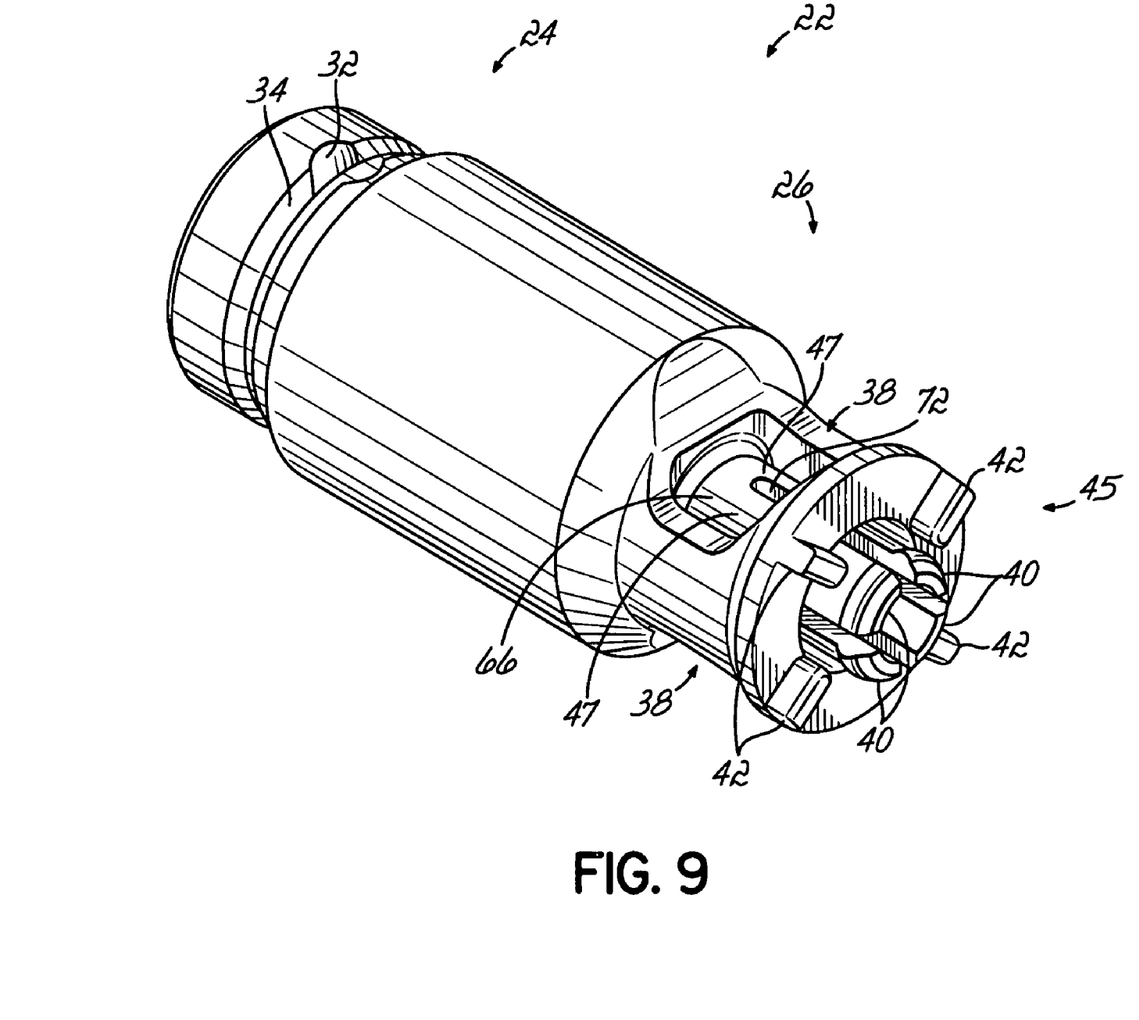
FIG. 9 is a perspective view of a distal end of the attachment piece of the surgical driver of FIG. 7.

Referring now to FIG. 9, the distal end 26 of the attachment piece 22 may have an open design. The open design is provided by openings 38 formed to facilitate cleaning of the attachment piece 22 and reduces the mass of the attachment piece 22. The distal end 26 of the attachment piece also includes mounting structure 45 configured to engage or receive an implant 200 (FIG. 13).

Figure 13:
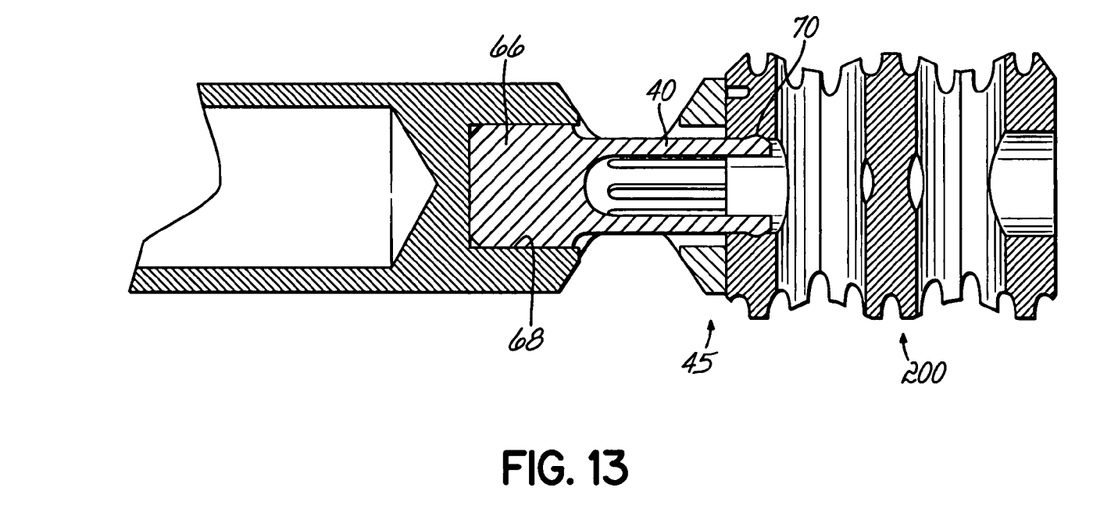
FIG. 13 is a partial, cross-sectional view of the attachment piece of FIG. 8, shown with an implant mounted to one embodiment of a retaining pin located at the distal end of the attachment piece.

In the illustrated embodiment, shown in FIG. 13, the mounting structure 45 includes a pin retainer 66 (see also FIG. 8). The pin retainer 66 is positioned within a bore 68 formed in the distal end 26 of the attachment piece 22. The pin retainer 66 has one or more arms or extensions 40 that reversibly or detachably connect to an implant 200. Although four substantially rectangular extensions 40 are depicted, any number of extensions 40 may be used, and any desired shape or configuration may be employed. The extensions 40 may include a projection 70 at a free end of the extension 40 that engage similar structure, such as a groove, formed in the implant 200. Preferably the extensions 40 are constructed so that the implant 200 can be attached and detached to the attachment piece 22 by a snap-fit connection, yet still provide a sufficient interference fit to securely retain the implant 200 during the surgical procedure.

Referring back to FIG. 9, a base 47 of each of the extensions 40 is accessible through the opening 38 of the attachment piece 22 in order to facilitate cleaning. That is, a slot or space 72 separates each of the extensions 40. The spaces 72 create a structural characteristic of the mounting structure 45 such that an implant can be easily mounted to the surgical driver 100. The openings 38 provide access to the spaces and extension components of the pin retainer 66 to facilitate cleaning.

Figure 14:
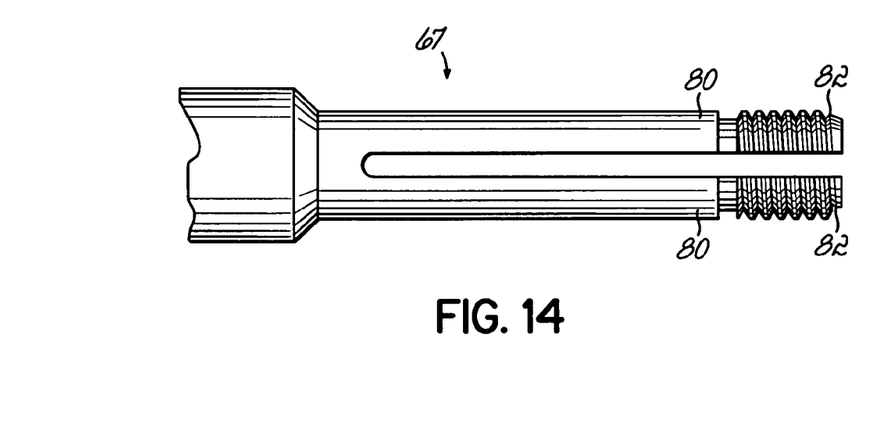
FIG. 14 is a side view of another embodiment of a retaining pin for use with the attachment piece of FIG. 13.

The pin retainer 66 may be permanently secured within the bore 68 of the attachment piece, or may be removable. In providing a removable pin retainer 66, different sizes and configurations of extensions 40 may be used with the surgical driver 100. For example, an alternative embodiment of a pin retainer 67 is illustrated in FIG. 14. This pin retainer 67 includes one or more extensions 80 having threaded ends 82 adapted to couple to or interface with a complimentarily adapted implant.

Referring back to FIG. 9, the distal end 26 of the attachment piece 22 may also include one or more alignment bars 42 to facilitate proper orientation of the implant 200. In one embodiment, the interface, including the extensions 40 of the pin retainer 66 and the alignment bars 42, between the attachment piece 22 and the implant 200 is a torque-transmitting coupling. The interface between the attachment piece 22 and the implant may be of any type, and is not intended to limit the scope of this invention.

In use, the variable-axis surgical driver 100 may be assembled and connected to an implant 200 in the order preferred by the operator. For instance, the implant 200 may be reversibly or detachably connected to the attachment piece 22, prior to the connection of the shaft 2 to the attachment piece 22, or this process may be reversed. The versatility with regard to the assembly of the surgical driver and integration with the implant is one advantage of the present disclosure.

Once the distal end 6 of the shaft 2 is aligned with the recess 28 of the attachment piece 22, the coupling arrangement 25 (e.g. the retaining member 30 of the attachment piece 22 and the indent 18 of the shaft 2) forms a reversible friction relationship. In this embodiment, the strength of the frictional relationship between, for example, the retainer 30 and the recess 28 can be adjusted through the use of a particular snap ring 37 having a desired tension. Once the knob 16 of the shaft 2 is positioned within the recess 28 and the friction relationship is established, the shaft 2 will have a predetermined degree of angular freedom about the longitudinal axis 50 of the attachment piece 22. The degree of angular freedom can be adjusted by providing a smaller recess 28 or a wider, deeper, or more elliptical indent 18. The degrees of freedom can also be adjusted by implementing various modifications to the relative shapes of facets 14, 15a, 15b, 17a, 17b, 19 and/or corresponding surfaces of recess 28.

In an alternative embodiment, a desired frictional relationship of the coupling arrangement 25 may be achieved between the shaft 2 and attachment piece 22, without the use of an indent and/or retainer. For instance, the relationship formed by the interaction of the shaft 2 with the recess 28 of the attachment piece 22 may be such that a desired degree of friction is achieved, while maintaining a desired degree of angular freedom.

Referring again to FIGS. 11 and 12, the angular freedom of the variable-axis surgical driver 100 is illustrated. In FIG. 11, the longitudinal axis 49 of the shaft 2 is shown in one of a plurality of variable-axis positions or orientations relative to the longitudinal axis 50 of the attachment piece 22. The facets 14 at the distal end 6 of the shaft 2 facilitate the angular freedom. Without the facets 14, a circumferential edge (not shown) of the distal end 6 of the shaft 2 would function as a fulcrum when the shaft 2 is tilted, possibly dislodging the knob 16 from its friction relationship with the recess 28. Therefore, the facets 14 advantageously facilitate the tilting of the shaft 2 without resulting in dislodgment. The relative sizes and shapes of the recess 28 and knob 16 as well as the shape and orientation of the facets 14 will together contribute to providing the desired level or degree of angular freedom of the shaft 2.

In applications where angular freedom is not desirable, the variable-axis surgical driver may include a device that fixes the axial orientation of the shaft 2 relative to the attachment piece 22. For example, a sleeve (not shown) having a length that extends along both the attachment piece and the shaft may be slid over then end of the driver 100 to maintain the relative axial position of both the shaft and attachment piece. Alternatively, a locking mechanism (not shown) can be used to lock the shaft and attachment piece in a coaxial position relative to one another, or an angular position relative to one another.

In one implant procedure using the surgical driver 100, an operator will connect the various components of the surgical driver and an implant according to a predetermined sequence. Once the desired components are connected to the implant, the implant 200 is positioned at a desired intervertebral area. As the implant is inserted, the coupling arrangement 25 of the surgical driver will provide a controllable relationship between the longitudinal axes of the surgical driver and the implant, will decrease the risk and/or amount of variable-axis torque that is applied to the implant, and will decrease the risk of damage to the implant during implantation and/or removal.

In particular, the ability to decrease and more effectively manage variable-axis torque, lessens the risk of implant fracture. Further, because of the ability to tilt the handle and shaft with respect to the implant, a more comfortable and more efficient grip can be maintained by an operator. Variable-axis freedom also will provide a better sightline to the implant. In particular, as the handle and first member is tilted, a direct line of sight to the attachment piece and implant is provided in a direction aligned with the longitudinal axis 50 of the attachment piece 22. Additionally, when two or more operators will be performing the implant procedure, the surgical driver 100 will be easily accessible from either side of the operating table.

Figure 15:
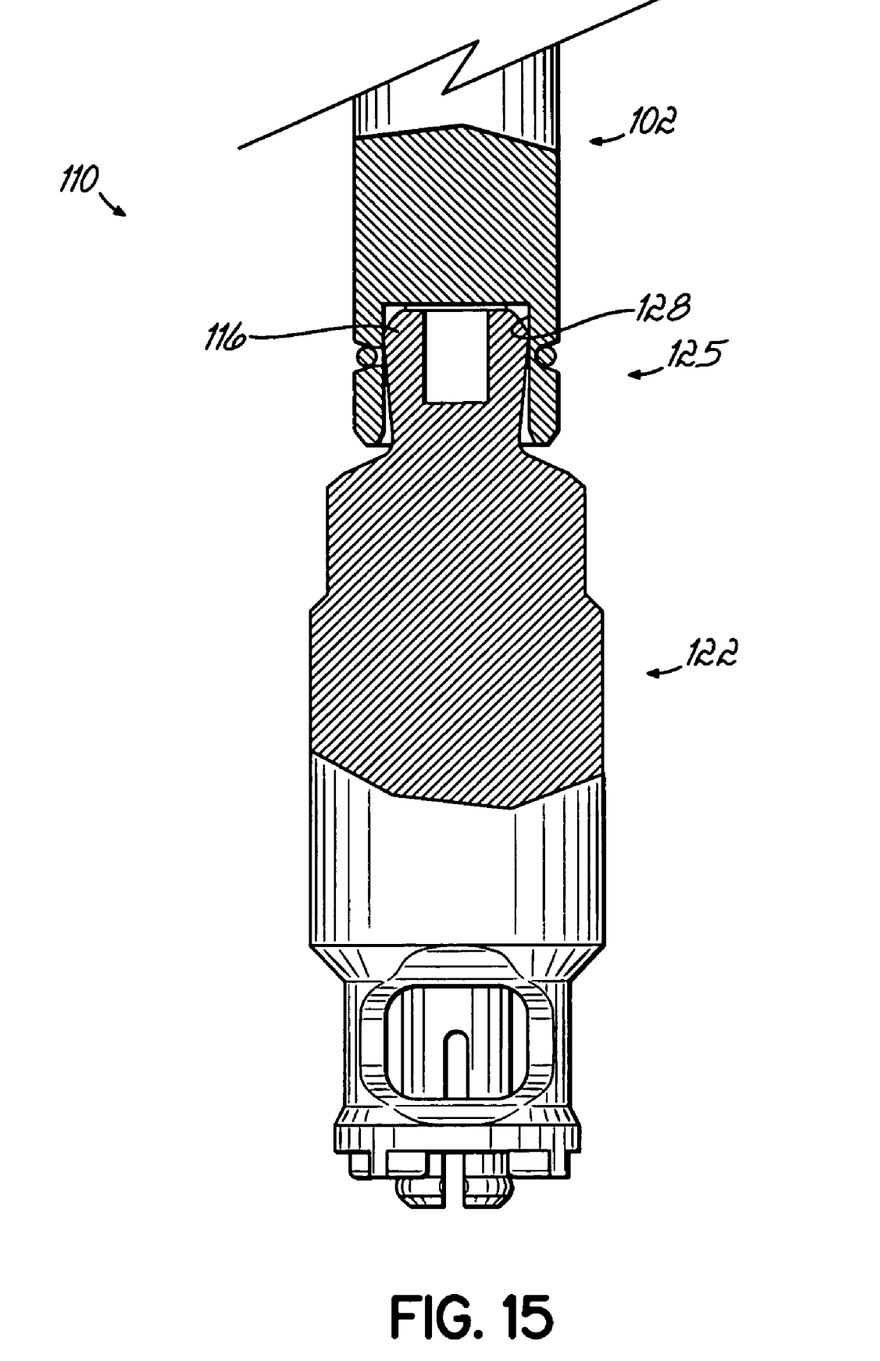
FIG. 15 is a partial, cross-sectional view of another embodiment of a surgical driver, in accord with the principles disclosed.

While the invention has been described with respect to the coupling arrangement 25 including the knob 16 of the shaft 2 coupling with the recess 28 of the attachment piece 22, a reversed arrangement is contemplated. Referring to FIG. 15, an alternative embodiment of a coupling arrangement 125 of another variable-axis surgical driver 110 is illustrated. In this embodiment, the coupling arrangement 125 of the surgical driver 110 includes a recess 128 formed in a shaft 102, and a knob 116 formed on an attachment piece 122. In accord with the principles disclosed, the alternative variable-axis surgical driver 110 includes similar features and advantages as those previously described.

The present disclosure of the surgical driver 100 has been described in use with an implant. As can be understood and in keeping with the principles disclosed, the surgical driver can be adapted for use with other surgical devices, such as distraction plugs, temporary implants, and other preparation devices, for example.

While the invention has been described with respect to a limited number of embodiments, those skilled in the art, having benefit of this disclosure, will appreciate that other embodiments can be devised which do not depart from the scope of the invention as disclosed herein.

We claim:

1. A surgical driver for use with an implant, the driver comprising:
   a) an attachment piece having mounting structure configured to engage an implant;
   b) a shaft connected to the attachment piece by a coupling arrangement, the coupling arrangement being configured to:
      i) transfer torque from the shaft to the attachment piece; and
      ii) permit the shaft to pivot relative to the attachment piece in a range of axial orientations relative to a longitudinal axis of the attachment piece in response to a side torque being applied to the shaft;
   c) wherein the coupling arrangement includes a recess formed in the attachment piece, the recess being configured to receive a distal end of the shaft, and further wherein the attachment piece includes a retaining member, at least a portion of the retaining member being positioned within the recess to detachably connect the shaft to the attachment piece; and
   d) a snap ring arranged to capture the retaining member within a bore formed in the attachment piece, the retaining member being moveable against the bias of the snap ring;
   e) wherein the retaining member is spring-loaded by the snap ring that biases the retaining member to project into the recess to contact the distal end of the shaft;
   f) wherein the retaining member is a ball.

2. The surgical driver of claim 1, wherein the plurality of axial orientations is in a range of 1 to 30 degrees, in any direction, relative to a longitudinal axis of the implant.

3. The surgical driver of claim 1, wherein the coupling arrangement includes one or more facets formed at a distal end of the shaft that permit the shaft to pivot in a range of axial orientations relative to a longitudinal axis of the attachment piece.

4. The surgical driver of claim 3, wherein the one or more facets are formed on a knob located at the distal end of the shaft.

5. The surgical driver of claim 4, further including one or more facets located adjacent to a base of the knob.

6. The surgical driver of claim 1, wherein one of the shaft and the attachment piece includes indicia to indicate a rotational orientation of an implant mounted on the attachment piece.

7. The surgical driver of claim 1, wherein the ball engages an indent formed in the distal end of the shaft when the distal end of the shaft is inserted into the recess of the attachment piece.

8. The surgical driver of claim 7, wherein the indent formed in the distal end of the shaft is elliptical.

9. The surgical driver of claim 1, wherein the coupling arrangement includes a recess formed in the shaft, the recess being configured to receive a proximal end of the attachment piece.

10. The surgical driver of claim 1, further including a torque-limiting mechanism.

11. The surgical driver of claim 1, wherein the attachment piece includes self-centering structure that axially aligns the shaft with the attachment piece when the shaft is initially connected to the attachment piece.

12. The surgical driver of claim 1, further including a handle coupled to a proximal end of the shaft.

13. The surgical driver of claim 12, wherein the handle includes a ratchet mechanism.

14. The surgical driver of claim 1, wherein the mounting structure of the attachment piece includes a pin structure having arms that extend outward from a distal end of the attachment piece.

15. The surgical driver of claim 14, wherein the arms provide a snap-fit connection for mounting an implant.

16. The surgical driver of claim 14, wherein the arms provide a threaded connection for mounting an implant.

17. The surgical driver of claim 14, wherein the pin structure is positioned within a bore formed in a distal end of the attachment piece, the pin structure being removable from the bore.

18. A surgical system, comprising:
   a) an implant;
   b) an attachment piece having mounting structure, the implant being secured to the mounting structure of the attachment piece;
   c) a shaft connected to the attachment piece by a coupling arrangement, the coupling arrangement being configured to:
      i) transfer torque from the shaft to the implant; and
      ii) permit the shaft to pivot relative to the implant in a range of axial orientations relative to a longitudinal axis of the attachment piece in response to a side torque being applied to the shaft;
   d) wherein the coupling arrangement includes a recess formed in the attachment piece, the recess being configured to receive a distal end of the shaft, and further wherein the attachment piece includes a retaining member, at least a portion of the retaining member being positioned within the recess to detachably connect the shaft to the attachment piece; and
   e) a snap ring arranged to capture the retaining member within a bore formed in the attachment piece, the retaining member being moveable against the bias of the snap ring;
   e) wherein the retaining member is spring-loaded by the snap ring that biases the retaining member to project into the recess to contact the distal end of the shaft;
   f) wherein the retaining member is a ball.

19. The surgical system of claim 18, wherein the plurality of axial orientations is in a range of 1 to 30 degrees, in any direction, relative to the implant.

20. The surgical system of claim 19, wherein the coupling arrangement includes one or more facets formed at a distal end of the shaft that permit the shaft to pivot in the range of axial orientations.

21. The surgical system of claim 18, wherein the coupling arrangement includes a recess formed in the shaft, the recess being configured to receive a proximal end of the attachment piece.

* * * * *